(12) United States Patent
Nelson

(10) Patent No.: US 8,988,680 B2
(45) Date of Patent: **\*Mar. 24, 2015**

(54) DUAL POLARIZATION WITH LIQUID CRYSTAL TUNABLE FILTERS

(71) Applicant: ChemImage Corporation, Pittsburgh, PA (US)

(72) Inventor: Matthew Nelson, Harrison City, PA (US)

(73) Assignee: ChemImage Technologies LLC, Pittsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/651,600

(22) Filed: Oct. 15, 2012

(65) Prior Publication Data

US 2013/0038877 A1 Feb. 14, 2013

Related U.S. Application Data

(63) Continuation-in-part of application No. 12/799,779, filed on Apr. 30, 2010, now Pat. No. 8,289,513.

(51) Int. Cl.
*G01J 3/28* (2006.01)
*G01J 3/02* (2006.01)
(Continued)

(52) U.S. Cl.
CPC .... *G01J 3/02* (2013.01); *G01J 3/32* (2013.01); *G01J 3/44* (2013.01); *G01N 21/314* (2013.01); *G01N 21/35* (2013.01); *G02B 21/0092* (2013.01); *G02B 21/16* (2013.01);
(Continued)

(58) Field of Classification Search
USPC .......................... 356/300, 326, 328, 317, 417
See application file for complete search history.

(56) References Cited

U.S. PATENT DOCUMENTS

| 4,749,257 A | 6/1988 | Klausz |
| 5,080,486 A | 1/1992 | Shirasaki |

(Continued)

FOREIGN PATENT DOCUMENTS

| WO | WO2006058306 | 6/2006 |
| WO | WO2008108846 | 9/2008 |

OTHER PUBLICATIONS

Kline, Nicole J. et al., Raman Chemical Imaging of Breast Tissue, Journal of Raman Spectroscopy, vol. 28, 119-124 (1997).
(Continued)

*Primary Examiner* — Abdullahi Nur
(74) *Attorney, Agent, or Firm* — Pepper Hamilton LLP

(57) ABSTRACT

A high passband transmission ratio is obtained by splitting a light beam from an objective lens into two orthogonally-polarized components processed along distinct paths through two independently controllable liquid crystal tunable filters (LCTFs). The filtered portions may be combined at an imaging plane or may be separately processed without recombining. Using two LCTFs, the arrangements discussed herein may ideally achieve 100% transmission in a single passband when two orthogonal components of a single wavelength are tuned, or 50% transmission at two distinct passbands when two orthogonal components from two different wavelengths (one component from each wavelength) are tuned. The dual polarization configuration described herein may be used to improve contrast or detected signal intensity in various microscopy and spectroscopic/chemical imaging applications and to increase the speed of detection.

28 Claims, 3 Drawing Sheets

(51) Int. Cl.
*G01J 3/32* (2006.01)
*G01J 3/44* (2006.01)
*G01N 21/31* (2006.01)
*G01N 21/35* (2014.01)
*G02B 21/00* (2006.01)
*G02B 21/16* (2006.01)
*G02B 21/36* (2006.01)
*G01N 21/21* (2006.01)
*G01N 21/33* (2006.01)
*G01N 21/3581* (2014.01)
*G01N 21/359* (2014.01)
*G01N 21/65* (2006.01)

(52) U.S. Cl.
CPC ............ *G02B 21/361* (2013.01); *G01J 3/0224* (2013.01); *G01N 21/21* (2013.01); *G01N 21/33* (2013.01); *G01N 21/3581* (2013.01); *G01N 21/359* (2013.01); *G01N 21/65* (2013.01)
USPC ........................................................ 356/326

(56) References Cited

U.S. PATENT DOCUMENTS

| | | |
|---|---|---|
| 5,097,352 A | 3/1992 | Takahashi |
| 5,321,539 A | 6/1994 | Hirabayashi |
| 5,657,121 A | 8/1997 | Nishina |
| 5,740,288 A | 4/1998 | Pan |
| 6,002,476 A | 12/1999 | Treado |
| 6,014,475 A | 1/2000 | Frisken |
| 6,262,851 B1 | 7/2001 | Marshall |
| 6,415,077 B1 | 7/2002 | Frisken |
| 6,522,467 B1 | 2/2003 | Li |
| 6,717,668 B2 | 4/2004 | Treado |
| 7,460,227 B1 | 12/2008 | Kim |
| 2003/0108284 A1 | 6/2003 | Danagher |
| 2004/0109232 A1 | 6/2004 | Riza |
| 2005/0015004 A1 | 1/2005 | Hertel |
| 2005/0148842 A1 | 7/2005 | Wang |
| 2005/0228452 A1 | 10/2005 | Mourlas |
| 2006/0119797 A1 | 6/2006 | Ockenfuss |
| 2008/0212180 A1 | 9/2008 | Zhang |
| 2010/0225899 A1 | 9/2010 | Treado |

OTHER PUBLICATIONS

Levenson, Richard, "Spectral Imaging and Pathology: Seeing More," Laboratory Medicine, Apr. 2004, vol. 35, pp. 244-251.

Levenson, Richard et al., "Multiplexing with multispectral Imaging: from Mice to Microscopy," available from: http://www.cri-inc.com/assets/nuance/MultiplexingwithMSIfrommicetomicroscopy.pdf, last accessed Nov. 23, 2010.

//DUAL POLARIZATION WITH LIQUID CRYSTAL TUNABLE FILTERS

RELATED APPLICATIONS

This Application is a continuation-in-part to pending U.S. patent application Ser. No. 12/799,779, filed on Apr. 30, 2010, entitled "System and Method for Component Discrimination Enhancement Based on Multispectral Addition Imaging," which is hereby incorporated by reference in its entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array ("FPA") detectors are typically employed. The choice of FPA detector is governed by the spectroscopic technique employed to characterize the sample of interest. For example, silicon (Si) charge-coupled device ("CCD") detectors or CMOS detectors are typically employed with visible wavelength fluorescence and Raman spectroscopic imaging systems, while indium gallium arsenide ("InGaAs") FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, wide-field spectroscopic imaging of a sample can be implemented by collecting spectra over the entire area encompassing the sample simultaneously using an electronically tunable optical imaging filter such as an acousto-optic tunable filter ("AOTF") or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR) wavelengths, long wave infrared wavelengths (LWIR), and to some overlapping ranges. These correspond to wavelengths of approximately 180-380 nm (UV), 380-700 nm (VIS), 700-2500 nm (NIR), 850-1800 nm (SWIR), 650-1100 nm (MWIR), 400-1100 (VIS-NIR) and 1200-2450 (LWIR).

A LCTF uses birefringent retarders to distribute the light energy of an input light signal over a range of polarization states. The polarization state of light emerging at the output of the LCTF is caused to vary as a function of wavelength due to differential retardation of orthogonal components of the light, contributed by the birefringent retarders. The LCTF discriminates for wavelength-specific polarization using a polarizing filter at the output. The polarizing filter passes the light components in the output that are rotationally aligned to the polarizing filter. The LCTF is tuned by adjusting the birefringence of the retarders so that a specific discrimination wavelength emerges in a plane polarized state, aligned to the output polarizing filter. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence; such differential retardation also amounts to a change in their polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer (i.e., the polarizing filter) at the output.

A filter as described is sometimes termed an interference filter because the components that have been divided and subdivided from the input and interfere positively at the output selection polarizer are the components that are passed. Such filters also are sometimes described with respect to a rotational twist in the plane polarization alignment of the discriminated component between the input and the selection polarizer at the output.

There are several known configurations of spectral filters comprising birefringent retarders, such as the Lyot, Solc and Evans types. Such filters can be constructed with fixed (nontunable) birefringent crystals for the retarders. A filter with retarders that are tuned in unison permits adjustment of the bandpass wavelength. Tunable retarders can comprise liquid crystals or composite retarder elements each comprising a fixed crystal and an optically aligned liquid crystal.

The thicknesses, birefringences, and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter (or "selection polarizer").

A spectral filter may have a comb-shaped transmission characteristic. Increasing or decreasing the birefringence when tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

A LCTF thus passes only one of two orthogonal components of input light. The transmission ratio in the passband is at a maximum for incident light at the input to the LCTF that is aligned to a reference angle of the LCTF. Transmission is at minimum for incident light energy at the input is orthogonal to that reference angle. If the input light in the passband is randomly polarized, the best possible transmission ratio in the passband is fifty percent. It is therefore desirable to devise a system and method wherein both orthogonal components of the input light are allowed to transmit through the tunable filter, thereby effectively doubling the throughput at the filter output.

SUMMARY

The present disclosure provides for techniques for dual beam processing through a plurality of LCTFs, including processing both orthogonal polarization components of the incident light at the input to the LCTF. The configuration provided herein overcomes the limitations of the prior art by maximizing the light transmission ratio during spectrally filtered imaging using the LCTF.

The present disclosure relates to a method for spectral imaging using two LCTFs sensitive to a polarization orientation of a light input beam from an objective lens, wherein the light input beam is to be spectrally filtered by the two LCTFs and coupled to at least one imaging lens. The method comprises: splitting the light input beam into a first and a second beams with respectively orthogonal polarization components; applying the first beam to a first one of the two LCTFs and the second beam to a second one of the two LCTFs such that a polarization component in each of the first and the second beams is filtered by a respective LCTF to transmit a corresponding passband wavelength; and arranging the imaging lens relative to filtered first and second beams at respective outputs of the two LCTFs so as to focus images from both of the filtered first and second beams. The present disclosure contemplates that the filtered beams may be displayed in either an overlaid or non-overlaid configuration. The present disclosure also contemplates that the beams may be displayed on a single detector or more than one detector.

It is an aspect of the disclosure that these techniques can be accomplished in a way that facilitates use of the LCTF in imaging applications. In that case, the two LCTFs can be oriented orthogonally relative to one another, and disposed to form an image through the same optics. The input light is split into its orthogonal plane polarized beams and each beam is aligned to the reference angle of one of the LCTFs. The resulting cross-polarized images are either overlaid on one another or displayed in a non-overlaid configuration.

In this embodiment, it is possible to tune the two adjacent LCTFs to the same passband, thereby maximizing the intensity of the passband at the photodetector array. Alternatively, the two adjacent LCTFs can be tuned to different passband wavelengths. In a case where a given material or object of interest is characterized by two wavelength peaks, simultaneously displaying the images at two distinct wavelengths on one or more detectors holds potential for increasing the speed of detection. For example, if two images are displayed simultaneously for a material or object characterized by two wavelength peaks, then the speed of detection becomes the frame rate of the camera. Such a configuration holds potential for detection in real time. In other embodiments where a material or object is characterized by n-number of wavelength peaks, then detection can be achieved in a shorter amount of time (for example, detection in half the time).

Alternative embodiments wherein the images are overlaid on each other holds potential or substantially increasing the contrast for that species in the composite image, even in the presence of other species that might be detectable at one but not both of the same wavelengths.

According to an aspect of this disclosure, an imaging system is provided with at least one imaging lens or lens assembly and a plurality of spectral filters that rely on polarization alignment. In particular, the spectral filter(s) can comprise one or more LCTFs. The optics can be infinitely corrected or the LCTF can be disposed at a focal plane. The objective lens collects light from a sample, for example laser-excited Raman radiation, and directs the light, for example as a collimated beam, to a LCTF. Such a filter is inherently sensitive to polarization state. Light emerging from the spectral filter is coupled through the imaging lens to be resolved on an image plane such as a CCD photosensor array.

As discussed above, in a conventional LCTF configuration, the output beam (i.e., the filtered output from the LCTF) is limited to one of two orthogonal polarization components of the collected light, which in the case of random polarization is 50% of the light power. However, the configurations of the present disclosure hold potential for increasing the intensity of the image at a photodetector array.

One polarization component of the light from the sample can be transmitted directly through a polarization beam splitter. This component is plane polarized and incident on the LCTF at the reference alignment of the LCTF. Therefore, this component is provided at the polarization alignment that obtains a maximum transmission ratio of the passband through the LCTF.

An alternative embodiment has two orthogonally aligned beam paths and two orthogonally aligned LCTFs. The input light is split into orthogonal beams as above. The two LCTFs are placed along laterally adjacent beam paths. One of the beam paths and LCTFs can operate as already described. The LCTF on the second beam path can be tuned to the same or a different wavelength. The LCTF on the second beam path can be oriented parallel to the first LCTF and preceded by a half wave plate at 45° so as to pre-orient the second beam. Or in another alternative, the half wave plate is omitted and the second LCTF is physically rotated ±90° from parallel to the first LCTF. When the LCTFs are tuned to the same wavelengths, the overlaid images are cross-polarized and image intensity at the detector is at the maximum. When the LCTFs are tuned to different wavelengths, the image intensities are at half maximum. However, the dual polarization configuration of the present disclosure holds potential for enhancing the contrast in a resulting image.

BRIEF DESCRIPTION OF THE DRAWINGS

There are shown in the drawings certain embodiments that are apt for use in explaining the methods and apparatus presented in this disclosure. However the extent of this disclosure is not limited to these examples but also encompasses variations and other equivalent embodiments within the scope of the description and as defined in the claims. The present disclosure will now be described for purposes of illustration and not limitation, in connection with the following figures, wherein:

DETAILED DESCRIPTION

Figure 1:
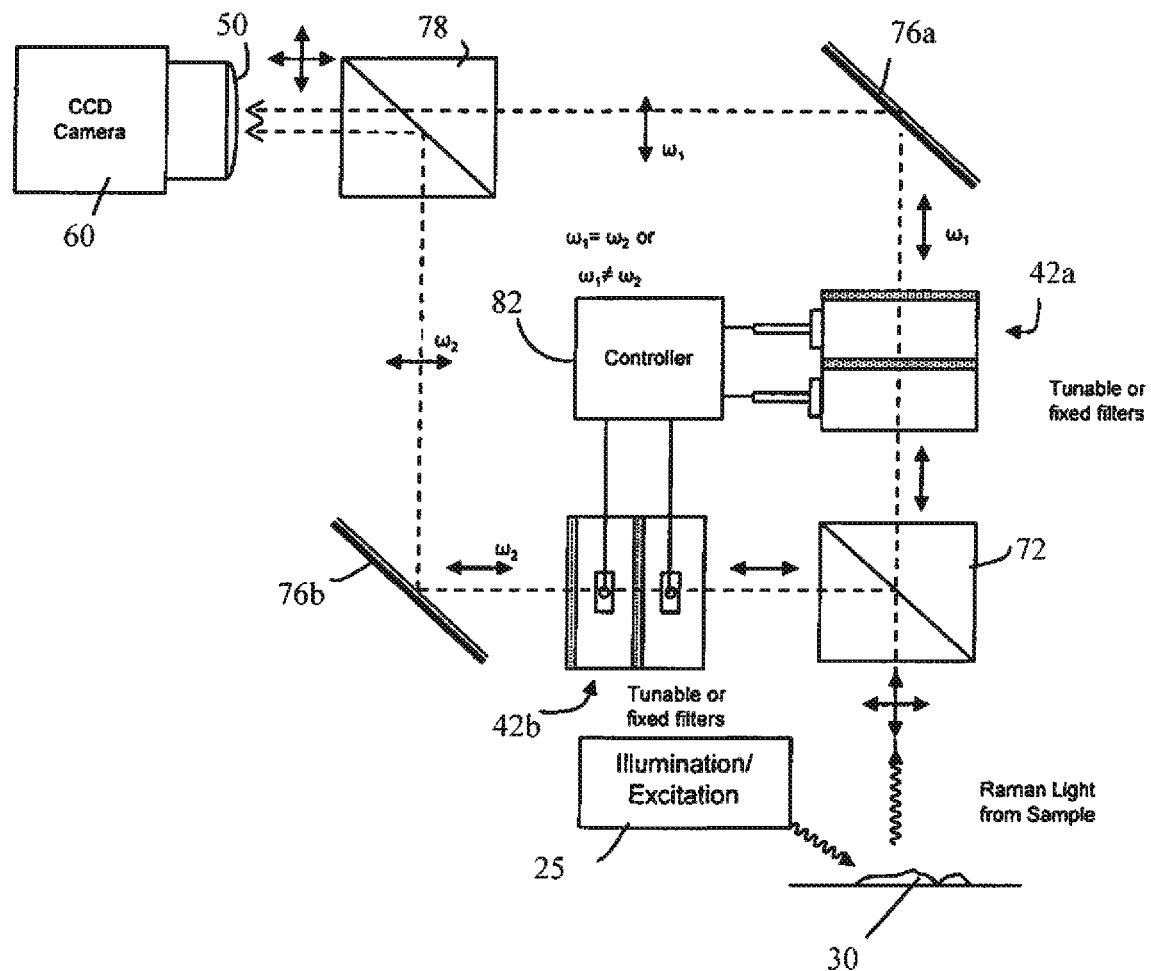
FIG. 1 is a schematic representation of a dual polarization configuration of the present disclosure.

Reference will now be made in detail to the embodiments of the present disclosure, examples of which are illustrated in the accompanying drawings. Wherever possible, the same reference numbers will be used throughout to refer to the same or like parts.

Light is transmitted through a LCTF, provided that the light is at one of the required discrimination wavelengths defined by the filter transmission characteristic (e.g., a comb filter) and has a predetermined polarization alignment relative to the filter. An input polarization beam splitter might be placed immediately preceding the filter such that only plane polarized light aligned to the necessary reference input polarization angle is admitted to the filter. However, such an input polarization beam splitter is optional because operation of the filter relies on and selects for both the necessary polarization alignment and the necessary wavelength at the input. Thus, the filter can only transmit light that is parallel to the input polarization angle.

Therefore, even light that is at the correct wavelength will be blocked by the LCTF if the polarization alignment of that light at the input to the LCTF is orthogonal to the predetermined input reference alignment of the LCTF. This has the adverse effect that if the input polarization orientation is random, then the maximum possible transmission ratio at the discrimination wavelengths is 50%.

The present disclosure provides polarization independent embodiments wherein the transmission ratio is substantially improved by parallel processing of originally orthogonal polarization components through a plurality of spectral filters.

Examples of polarization dependent spectral filters include the Lyot, Evans and Solc birefringent filter configurations, originally developed for astrophysical spectral analysis. There are three kinds of basic configurations of stacked polarization interference filters: Lyot filter, Evan split-element filter and Solc filter. The Lyot polarization interference filter was introduced by B. Lyot in 1933 (see, B. Lyot, *Comptes Rendues* 197, 1593 (1933)). A basic Lyot filter comprises a number of filter stages. Each stage consists of a fixed retarder bounded by linear polarizers. Another stacked polarization interference filter is the Evans split-element filter (see, J. W. Evans, *J. Opt. Soc. Am.* 39, 229 (1949)), wherein two stages of Lyot filter may be combined into a single stage. In the Evans split-element filter, to eliminate a stage, the birefringent element for the stage to be eliminated is split in half and the split elements are positioned on either side of the birefringent element of another stage. In the Evan filter, the polarizers are crossed, and the center birefringent element is oriented parallel to either polarizer. Based on the configuration of Evans split-element filter, the U.S. Pat. No. 6,091,462 provides split-element liquid crystal filters in wide-field, bandpass, cut-on, cut-off and notch filter embodiments. Another basic configuration of a stacked polarization interference filter is the Solc filter (see, Solc, *J. Opt. Soc. Am.* 55, 621 (1965)). Solc filter uses a cascade of identical phase retarders in each stage without the need for polarizers between each of the retarders. Solc filter has two kinds of configurations: Solc fan arrangement and Solc folded arrangement. The first configuration, Solc fan filter, has N identical retarders in each stage—with the rotation angles of $\theta$, $3\theta$, $5\theta$, ... $(2N-1)\theta$—located between parallel polarizers, where $\theta=\pi/4N$. Another configuration, Solc folded filter, has N identical retarders in each stage with the optical axis of each retarder at $\pm\theta°$ with respect to the entrance polarizer. In the Solc folded filter, the retarders are located between crossed polarizers.

Tunable versions of spectral filters have been developed that include liquid crystal elements capable of being adjusted to determine filter bandpass wavelengths. LCTFs with cascaded stages are disclosed, for example, in U.S. Pat. No. 6,992,809—Wang, et al., the disclosure of which is hereby incorporated by reference in its entirety. The U.S. Pat. No. 6,992,809 discloses embodiments of bandpass filters (which may be referred to as multi-conjugate filters (MCFs)) that may use the Solc filter configurations, e.g., the Solc fan configuration and/or the Solc folded configuration.

LCTFs are designed by using liquid crystal materials as the birefringent elements or using liquid crystal materials as tunable retarders combined with fixed retarders. In the configurations (Lyot, Evan split-element, and Solc) described above, it is observed that LCTFs are sensitive to the polarization state of incident light.

LCTFs are inherently sensitive to the polarization state of incident light and capture only one polarization of light, thereby immediately losing one half of the available light. In the discussion herein below, LCTFs may include, but are not limited to, the multi-conjugate filters (MCFs) designed by ChemImage Corporation of Pittsburgh, Pa., or any other polarization interference filter based configuration e.g., the Lyot filter, the Evans split-element filter, the Solc filter, or a filter configuration based on one or more of these filters). Furthermore, although the discussion below is provided in the context of an LCTF, it is observed here that various methodologies discussed herein may be implemented in filter configurations that may not be liquid crystal based or that may not be tunable filter configurations. For example, one embodiment may comprise the use of one or more fixed filters. Examples of other filters contemplated by the present disclosure may include: multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof.

Referring now to FIG. 1, the sample 30 may be illuminated and/or excited by an illumination source 25. In one embodiment, the illumination source 25 may comprise a laser. In another embodiment, the illumination source may comprise a passive illumination source such as solar radiation. In one embodiment, it is possible to illuminate the sample from a laser directly in an oblique direction.

The embodiment of FIG. 1 comprises two independently tunable LCTFs 42a, 42b along distinct orthogonal beam paths for the orthogonal polarization components emerging from polarizing cube 72. In one embodiment, the LCTFs may comprise at least one of: a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof. In this arrangement, the paths of the filtered beams are not parallel through the LCTFs 42a, 42b, but are directed by appropriate reflectors (e.g., mirrors) 76a, 76b to a beam combiner 78 (which may be a polarizing cube or polarizing beam splitter as illustrated) at which the orthogonal components, which can be at the same or different passband wavelengths $\omega_1$ and $\omega_2$. In one embodiment, the components may be combined and directed to the a detector 60 through a lens assembly 50. In another embodiment, the components may be keeps separate as they are directed to the detector 60. However, the beam paths from one beam splitter 72 to the other 78 (via individual LCTFs 42a, 42b) may be made symmetrical to avoid, for example, need for infinitely-corrected optics.

In FIG. 1, the detector 60 is illustrated as comprising a CCD detector. However, the present disclosure contemplates that the detector 60 may comprise other detectors including but not limited to: a CCD, a complementary metal-oxide-semiconductor (CMOS) detector, an indium gallium arsenide (InGaAs) detector, a platinum silicide (PtSi) detector, indium antimonide (InSb) detector, a mercury cadmium telluride (HgCdTe) detector, and combinations thereof.

In FIG. 1, the two LCTFs 42a, 42b may be tuned in unison to the same wavelengths ($\omega_1=\omega_2$) using an LCTF controller 82. It is possible to configure the controller 82 to independently tune the passband wavelengths $\omega_1$ and $\omega_2$ of the LCTFs 42a, 42b that respectively process orthogonal components of the input. Therefore, by appropriate control, the LCTFs can be tuned to the same wavelength or to two different passband wavelengths ($\omega_1 \neq \omega_2$) at the same time. The controller 82 may be programmable or implemented in software to allow a user to selectively tune each LCTF 42a, 42b as desired.

Figure 2:
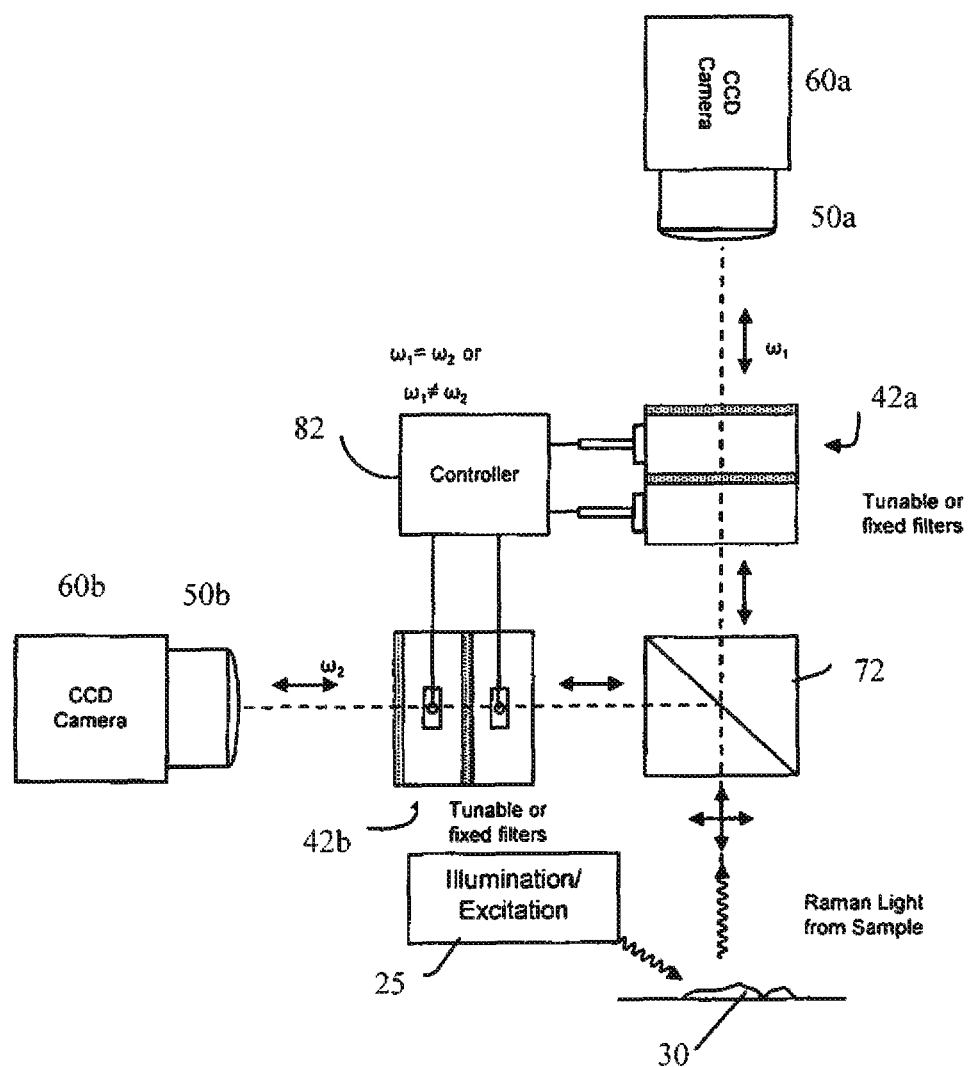
FIG. 2 is a schematic representation of a dual polarization configuration of the present disclosure.

In the embodiment of FIG. 1, a fast switching mechanism (not shown) may be provided to switch between the two views (or spectral images) corresponding to spectral data collected by the detector 60 from each of the tunable filter 42a, 42b. Alternatively, such two spectral views or images (from two separate LCTFs) may be combined or overlaid into a single image, for example, to increase contrast or intensity or for comparison purposes. The embodiment in FIG. 1 is shown to include a single CCD detector 60 to capture the filtered signals received from the LCTFs 42a, 42b. In another embodiment, the beam combiner 78 may be removed and two detectors cameras may be used. An exemplary embodiment of such a configuration is illustrated in FIG. 2. Each detector 60a and 60b may be optically coupled to a corresponding one of the two LCTFs 42a, 42b to capture filtered signals from the LCTF and to responsively generate electronic signals that enable display of spectral images of the illuminated sample 30. The present disclosure contemplates that any number of optical filters and associated detectors may be used to achieve the benefit of dual polarization as described herein.

In one embodiment, the two filtered signals may be detected simultaneously. As discussed herein, simultaneous detection of two different wavelengths holds potential for real-time detection when displayed in a non-overlapping configuration (side-by-side, top to bottom, etc.). In another embodiment, the two filtered signals may be detected sequentially.

It is noted here that although laser light may be coherent, the light received from the sample 30 (e.g., light emitted, scattered, absorbed, and/or reflected) and fed to the LCTFs 42a, 42b may not be coherent. Therefore, wavefront errors may not be present or may be substantially avoided in the two LCTF versions in FIGS. 1 and 2 because of processing of non-coherent light by each LCTF 42a, 42b.

Figure 3:
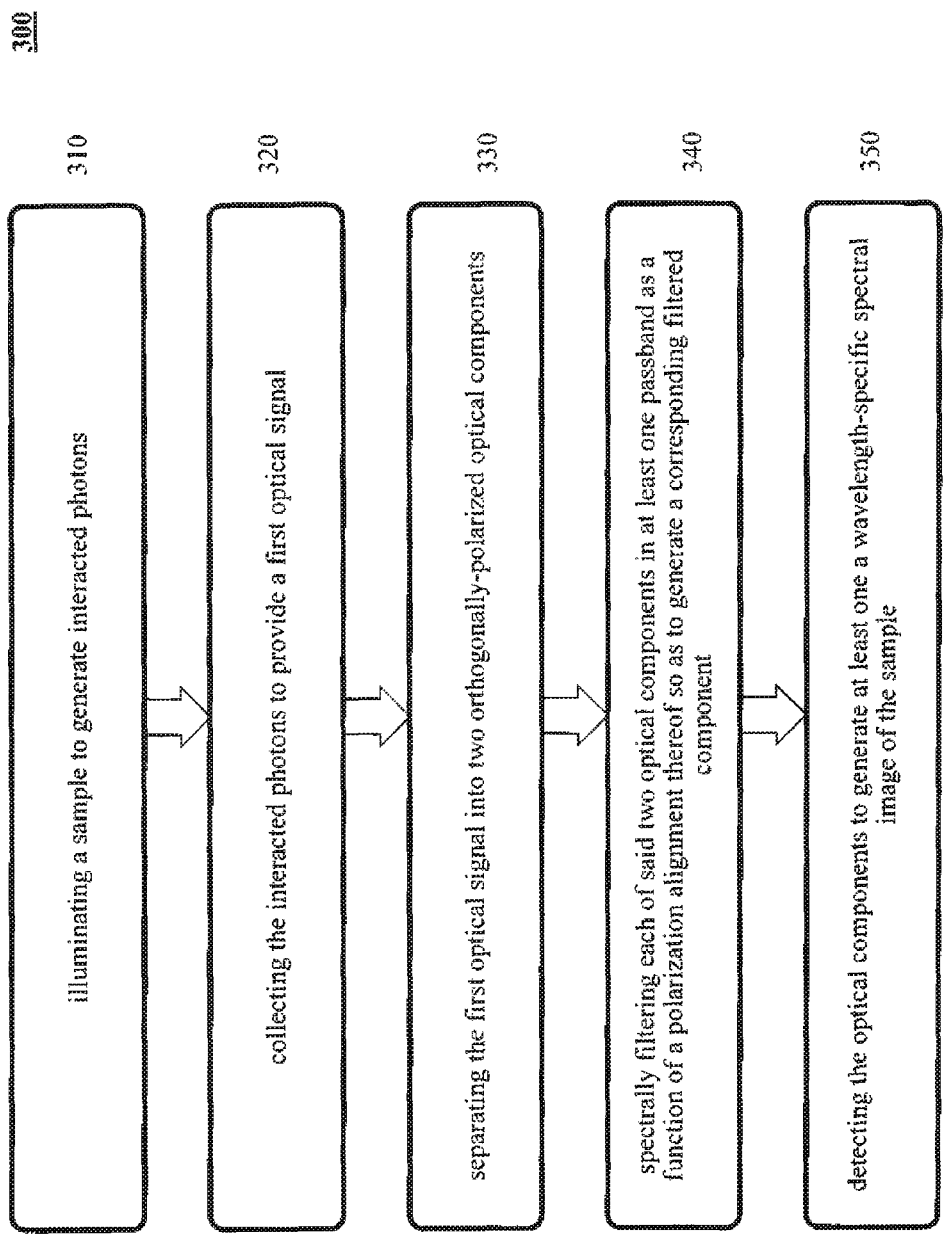
FIG. 3 is illustrative of a method of the present disclosure.

The present disclosure also provides for a method, one embodiment of which is illustrated in FIG. 3. The method 300 may comprise illuminating a sample to generate interacted photons in step 310. In step 320, the interacted photons may be collected to provide a first optical signal. In step 330, the first optical signal may be separated into two orthogonally-polarized components. The components may then be filtered by a corresponding optical filter to generate a filtered component in step 340. Each filtered component may be detected in step 350 to generate at least one wavelength-specific spectral image of the sample. In one embodiment, the image may comprise at least one of: a Raman image, a fluorescence image, an infrared image, a visible image, an ultra violet image, a laser induced breakdown spectroscopic (LIBS) image, and combinations thereof. In one embodiment, the infrared image may comprise at least one of: a near infrared image, a short wave infrared image, a mid wave infrared image, a long wave infrared image, and combinations thereof.

The present disclosure may be embodied in other specific forms without departing from the spirit or essential attributes of the disclosure. Although the foregoing description is directed to the embodiments of the disclosure, it is noted that other variations and modifications will be apparent to those skilled in the art, and may be made without departing from the spirit of scope of the disclosure.

What is claimed is:

1. An optical filter unit comprising:
    a first polarization assembly configured to:
        (i) receive a first optical signal comprising optical components in a plurality of polarization alignments,
        (ii) separate the first optical signal into a first optical component and a second optical component, and
        (iii) transmit the first optical component with a first polarization alignment and the second optical component with a second polarization alignment;
    a first optical filter configured to receive the first optical component and transmit at least a portion of the first optical component having a first wavelength;
    a second optical filter configured to receive the second optical component and transmit at least a portion of the second optical component having a second wavelength; and
    at least one detector configured to detect the first optical component and the second optical component.

2. The optical filter unit of claim 1, further comprising a first detector configured to detect the first optical component and a second detector configured to detect a second optical component.

3. The optical filter unit of claim 1, wherein the detector is configured to detect both the first optical component and the second optical component.

4. The optical filter unit of claim 1, further comprising a display configured to display the first optical component and the second optical component in an overlaid configuration.

5. The optical filter unit of claim 1, further comprising a display configured to display the first optical component and the second optical component in a non-overlaid configuration.

6. The optical filter unit of claim 1, wherein the first wavelength and the second wavelength are the same.

7. The optical filter unit of claim 1, wherein the first wavelength and the second wavelength are different.

8. The optical filter unit of claim 1, further comprising a second polarization assembly configured to combine the first optical component and the second optical component.

9. The optical filter unit of claim 1, wherein at least one of the first optical filter and the second optical filter is rotated to match orthogonally polarized light transmitted from the first polarization assembly.

10. The optical filter unit of claim 1, wherein at least one of the first optical filter and the second optical filter further comprise a tunable filter.

11. The optical filter unit of claim 10, wherein the tunable filter further comprises one or more of a liquid crystal tunable filter, a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof.

12. The optical filter unit of claim 1, wherein at least one of the first optical filter and the second optical filter further comprise a fixed filter.

13. The optical filter unit of claim 1, wherein the at least one detector comprises one or more of a CCD, a CMOS detector, an InGaAs detector, a PtSi detector, an InSb detector, a HgCdTe detector, and combinations thereof.

14. The optical filter unit of claim 1, wherein the first optical component and the second optical component are detected simultaneously.

15. The optical filter unit of claim 1, wherein the first optical component and the second optical component are detected sequentially.

16. The optical filter unit of claim 1, further comprising at least one additional optical filter and at least one additional detector configured to detect additional optical components from the optical signal.

17. An optical filter unit comprising:
a first polarization assembly configured to:
  (i) receive a first optical signal comprising optical components in a plurality of polarization alignments,
  (ii) separate the first optical signal into a first optical component and a second optical component, and
  (iii) transmit the first optical component with a first polarization alignment and the second optical component with a second polarization alignment;
a first optical filter configured to receive the first optical component and transmit at least a portion of the first optical component having a first wavelength;
a second optical filter configured to receive the second optical component and transmit at least a portion of the second optical component having a second wavelength, wherein the second wavelength is different from the first wavelength;
at least one detector configured to detect the first optical component and the second optical component, wherein the first optical component and the second optical component are detected simultaneously; and
a display configured to display the first optical component and the second optical component in a non-overlaid configuration.

18. A method comprising:
illuminating a sample to generate interacted photons;
collecting the interacted photons to generate an optical signal;
separating the optical signal into a first optical component and a second optical component;
transmitting the first optical component to a first optical filter and the second optical component to a second optical filter;
spectrally filtering the first optical component and the second optical component in at least one passband as a function of a polarization alignment to generate a corresponding filtered component; and
detecting the filtered components to generate at least one wavelength-specific spectral image of the sample.

19. The method of claim 18, wherein the first optical filter and the second optical filter each comprise a tunable filter where each filter is independently controllable, and wherein the method further comprises controlling the first optical filter and the second optical filter to a same corresponding passband wavelength.

20. The method of claim 18, wherein the first optical filter and the second optical filter each comprise a tunable filter where each filter is independently controllable, and wherein the method further comprises controlling the first optical filter and the second optical filter to a different corresponding passband wavelength.

21. The method of claim 18, wherein at least one of the first optical filter and the second optical filter comprise a tunable filter.

22. The method of claim 21, wherein the tunable filter comprises one or more of a liquid crystal tunable filter, a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof.

23. The method of claim 21, wherein the first optical component and the second optical component are detected simultaneously.

24. The method of claim 18, wherein the first optical component and the second optical component are detected sequentially.

25. The method of claim 18, wherein the wavelength-specific spectral image comprises at least one wavelength-specific spectral image of the first optical component and at least one wavelength-specific spectral image of the second optical component.

26. The method of claim 25, further comprising displaying the at least one wavelength-specific spectral image of the first optical component and the at least one wave-length specific spectral image of the second optical component in an overlaid configuration.

27. The method of claim 25, further comprising displaying the at least one wavelength-specific spectral image of the first optical component and the at least one wave-length specific spectral image of the second optical component in non-overlaid configuration.

28. The method of claim 21, further comprising generating at least one wavelength-specific image representative of a plurality of additional optical components associated with the optical signal.

* * * * *